United States Patent
Yang et al.

(10) Patent No.: US 9,233,897 B2
(45) Date of Patent: Jan. 12, 2016

(54) HFO-1234ZE AND HFC-245FA CO-PRODUCTION PREPARATION PROCESS

(71) Applicants: SINOCHEM MODERN ENVIRONMENTAL PROTECTION CHEMICALS (XI'AN) CO., LTD., Xi'an, Shaanxi (CN); Sinochem Lantian Co., Ltd., Zhejiang (CN)

(72) Inventors: Gang Yang, Shaanxi (CN); Huie Yang, Shaanxi (CN); Lei Xu, Shaanxi (CN); Hua Chai, Shaanxi (CN); Xintang Zhao, Shaanxi (CN); Wenqing Zhang, Shaanxi (CN); Changhua Zeng, Shaanxi (CN); Jianping Fan, Shaanxi (CN); Shaohua Yan, Shaanxi (CN); Kunfeng Liu, Shaanxi (CN); Zhong Li, Shaanxi (CN); Shukang Chen, Shaanxi (CN)

(73) Assignees: SINOCHEM MODERN ENVIRONMENTAL PROTECTION CHEMICALS (XI'AN) CO., LTD., Xi'an, Shaanxi (CN); SINOCHEM LANTIAN CO., LTD., Zhejiang (CN)

( * ) Notice: Subject to any disclaimer, the term of this patent is extended or adjusted under 35 U.S.C. 154(b) by 0 days.

(21) Appl. No.: 14/654,247

(22) PCT Filed: Dec. 17, 2013

(86) PCT No.: PCT/CN2013/089642
§ 371 (c)(1),
(2) Date: Jun. 19, 2015

(87) PCT Pub. No.: WO2014/094590
PCT Pub. Date: Jun. 26, 2014

(65) Prior Publication Data
US 2015/0321979 A1 Nov. 12, 2015

(30) Foreign Application Priority Data

Dec. 19, 2012 (CN) .......................... 2012 1 0554497

(51) Int. Cl.
*C07C 17/25* (2006.01)
*C07C 19/08* (2006.01)
*C07C 17/383* (2006.01)
*C07C 17/20* (2006.01)
*C07C 17/358* (2006.01)

(52) U.S. Cl.
CPC ............. *C07C 17/383* (2013.01); *C07C 17/206* (2013.01); *C07C 17/25* (2013.01); *C07C 17/358* (2013.01); *C07C 17/20* (2013.01); *C07C 19/08* (2013.01)

(58) Field of Classification Search
CPC .......... C07C 17/20; C07C 17/25; C07C 19/08
USPC .......................... 570/156, 170, 157, 166, 167
See application file for complete search history.

(56) References Cited

U.S. PATENT DOCUMENTS 5,986,151 A * 11/1999 Van Der Puy ........... C07C 17/25
570/156
6,124,510 A *  9/2000 Elsheikh ................. C07C 17/25
570/156

* cited by examiner

*Primary Examiner* — Elvis O Price
(74) *Attorney, Agent, or Firm* — Osha Liang LLP

(57) ABSTRACT

Disclosed is an HFO-1234ze and HFC-245fa co-production preparation method. The HFO-1234ze and HFC-245fa are prepared through a two-stage gas phase fluorination reaction by using 1,1,1,3,3-pentachloropropane (HCC-240fa) as a raw material. With the processing method of the present invention, HFO-1234ze and HFC-245fa can be prepared at the same time, and the alkene is unlikely to polymerize or carbonize during the reaction, thus being suitable for industrialized promotion.

24 Claims, 2 Drawing Sheets

HFO-1234ZE AND HFC-245FA CO-PRODUCTION PREPARATION PROCESS

TECHNICAL FIELD

The present invention relates to methods for preparing fluoroalkene, particularly relates to HFO-1234ze and HFC-245fa co-production methods.

BACKGROUND TECHNOLOGY

HFC-134a ($CF_3CH_2F$, 1,1,1,2-tetrafluoroethane) is currently the most widely used coolant. Even though its ozone destroying potential (ODP) is zero, its global warming potential (GWP) is high and can remain in the atmosphere for a long time. When used in large quantity, it can cause global warming. Therefore, European Union passed the F-gas regulations in 2006, banning uses of fluorinated gas with GWP greater than 150 as coolants in the air conditioners in new cars from Jan. 1, 2011, and banning use of fluorinated gas with GWP greater than 150 as coolants in all new automotive air conditioners from Jan. 1, 2017.

In the search for a substitute for HFC-134a, 1,3,3,3-tetrafluoropropene (HFO-1234ze) is recognized as a future substitute for HFC-134a as a new generation coolant, because its various properties, including ODP=0 and GWP<100. HFO-1234ze is also thought to be promising as a next generation foaming agent. In addition, it can be used as a cleaning agent, aerosol propellant, solvent composition, insulation material, and fire extinguishing and flame retarding agent, etc. Its applications are wide and promising.

1,1,1,3,3-Pentafluoropropane (HFC-245fa) is being developed as an ultimate substitute for the widely used foaming agent trichlorofluromethane (CFC-11) and its transition substitute product 1,1-dichloro-1-fluroethane (HCFC-141b). It is recognized as the most promising third generation foaming agent substitute. In addition, HCFC-245fa is used as a coolant, cleaning agent, aerosol agent, a starting material for other fluorinated compounds, heat conducting medium, tobacco swelling agent, and extraction agent, etc. Its application is broad and wide.

Currently, industrial methods for the preparation of HCFC-245fa mainly involve gas phase fluorination of 1,1,1,3,3-pentafluropropane. And, the preparation methods for HFO-1234ze mainly use 1-chloro-3,3,3-trifluoropropene (HCFC-1233 zd) and 1,1,1,3,3-pentachloropropane (HCC-240fa) as the starting materials. For example, Japanese patent No. JP10007604 discloses methods using Cr, Ti, Ni, Al, Mn, Co etc. metal oxides supported on carbon as catalysts to fluorinate HCFC-1233zd to produce HFO-1234ze. These methods have relatively high one-way conversion rate. U.S. Patent publication No. 2005/0020862 and Chinese Patent application No. CN1852880 disclose methods that under the catalysis of a fluorination catalyst, fluorinate the starting material 1-chloro-3,3,3-trifluoropropene (HCFC-1233zd) to produce 1-chloro-1,3,3,3-tetrafluoropropane and 1,1,1,3,3-pentafluoropropane. Then, in liquid phase under the action of a strong base to remove HF and produce HFO-1234ze. Chinese Patent No. CN1852880A, Japanese Patent Nos. JP10007605, JP 11140002, and U.S. Pat. Nos. S6,124,510, 5,986,151, etc. disclose a method that, under the action of a suitable catalyst, dehydrofluorinate 1,1,1,3,3-pentafluoropropane to produce HFO-1234ze. This method has a relatively high one-way conversion rate. Chinese Patent Publication No. CN200710090535.2 and CN200810000765.X reported a method that converts 1,1,1,3,3-pentachloropropane, under the action of a fluorination catalyst, to HFO-1234ze. This method first fluorinates 1,1,1,3,3-pentachloropropane to produce HCFC-1233zd and a small amount of HFC-245fa. Then, without purification, the mixture is placed into a second fluorination reaction to produce HFO-1234ze. The product is separated by a distillation column to produce HFO-1234ze. The unreacted HCFC-1233zd and HFC-245fa are circulated back into the second reactor.

In the industrial production, HFC-245fa is mainly prepared in liquid phase, and HFO-1234ze is mainly prepared in gas phase. Production of HFC-245fa in the liquid phase generates a large amount of waste liquid and the production often cannot be continuous. And, in the gas phase production of HFO-1234ze, HFC-245fa is a side product, which would need to be further dehydrofluorinated. The dehydrofluoroination reaction tends to inactivate the catalysts. The present invention provides methods for co-producing HFO-1234ze and HFC-245fa. These methods can overcome the deficiency in the art and product two useful products at the same time.

SUMMARY OF THE INVENTION

Embodiments of the invention provide methods for co-producing HFO-1234ze and HFC-245fa.

To accomplish the object of the invention, the invention involves the following embodiments.

A method for co-producing HFO-1234ze and HFC-245fa, characterized in that the method comprises the following steps:

(1) introducing into the first reactor (1) a starting material stream containing anhydrous HF and HCC-240fa (10). In the presence of an oxidative gale, under the action of a fluorination catalyst, the starting material anhydrous HF and HCC-240fa react to produce a product stream (11);

(2) introducing the product stream (11) into the first separation tower (2). A material stream (12) containing HCl is formed at the top of the separation tower. A material stream (13) containing HFC-245fa, HCFC-1233zd and HF is formed in the boiler of the separation tower;

(3) introducing material stream (13) into the second reactor (3). At the same time, pass an oxidative gas (14) into the second reactor (3). Under the action of a fluorination catalyst, the reaction continues and produces a product stream (15);

(4) delivering the product stream (15) into the second separation tower (4). A material stream (16) containing HCl and trans-HFO-1234ze is formed at the top of the separation tower. The material stream (16), after washing with water, is distilled and dried to produce trans-HFO-1234ze. A material stream (17) containing cis-HFO-1234ze, HFC-245fa, HCFC-1233zd, HCFC-244fa, and HF is formed in the boiler of the separation tower;

(5) introducing the material stream (17) into a static can (5). After the layers separate, the upper layer is a material flow (18), which primarily comprises HF, is circulated into reactor (1). The lower layer is an organic phase that forms a material stream (19) that comprises cis-HFO-1234ze, HFC-245fa and HCFC-1233zd;

(6) introducing the material stream (19) into the third separation tower (6). A material stream (20) formed at the top of the separation tower comprises primarily cis-HFO-1234ze. A material stream (21) formed in the boiler of the separation tower comprises HFC-245fa and HCFC-1233zd. The material stream (20), after isomerization, produces trans-HFO-1234ze;

(7) introducing the material stream (21) into the fourth separation tower (7). A material stream (22) formed at the top of the tower comprises HFC-245fa. A material stream (23) formed in the boiler of the separation tower comprises HCFC- 1233zd. The material stream (23) is circulated back into the first separation tower (2) or the second reactor (3).

In the first reactor (1), the reaction temperature is preferably 200-250° C., the reaction pressure is preferably 0.2-0.8 Mpa, the molar ratio of HF to HCC-240fa is preferably from 3:1 to 18:1, the gas flow speed is preferably 300-1000 $h^{-1}$. In more preferred embodiments, the reaction temperature is preferably 180-260° C., the reaction pressure is preferably 0.2-0.5 Mpa, the molar ratio of HF to HCC-240fa is preferably from 6:1 to 18:1, the gas flow speed is preferably 300-800 $h^{-1}$.

In the second reactor (3), the reaction temperature is preferably 300-380° C., the reaction pressure is preferably 0.2-0.8 Mpa, the molar ratio of HF to HCC-240fa is preferably from 3:1 to 8:1, the gas flow speed is preferably 300-800 $h^{-1}$.

In the first separation tower (2), the separation pressure is preferably 0.2-0.8 Mpa, and the separation temperature is preferably 50-100° C. More preferably, in the first separation tower (2), the separation pressure is the same as the reaction pressure in the first reactor (1), the separation pressure is 0.3-0.5 Mpa, and the separation temperature is 60-80° C. The top of the first separation tower (2) is preferably cooled with a coolant, and the temperature of the coolant is preferably −40-−20° C.

In the second separation tower (4), the separation pressure is preferably 0.2-0.8 Mpa, and the separation temperature is preferably 50-90° C. More preferably, in the second separation tower (4), the separation pressure is the same as the reaction pressure in the first reactor (1), the separation pressure is 0.3-0.5 Mpa, and the separation temperature is 50-70° C. The top of the second separation tower (4) is preferably cooled with a coolant, and the temperature of the coolant is preferably −50-−30° C.

In the third separation tower (6), the separation pressure is preferably 0.1-1.2 Mpa, and the separation temperature is preferably 50-100° C. The top of the third separation tower (6) is preferably cooled with a coolant, and the temperature of the coolant is preferably 0-20° C.

In the fourth separation tower (7), the separation pressure is preferably 0.2-0.9 Mpa, and the separation temperature is preferably 60-110° C. The top of the third separation tower (6) is preferably cooled with a coolant, and the temperature of the coolant is preferably 10-18° C.

The present invention provides a method for isomerization. The material stream (20) is introduced into the third reactor (8). Under the action of an isomerization catalyst, the isomerization occurs to produce a material stream (26) comprising trans-HFO-1234ze and cis-HFO-1234ze. The material stream (26) is introduced into the fifth separation tower (9). After separation, a material stream (25) comprising trans-HFO-1234ze is obtained at the top of the separation tower. A material stream (24) comprising cis-HFO-1234ze is obtained in the boiler of the separation tower. The material stream (24) is circulated into the third reactor (8).

In the third reactor (8), the reaction temperature is preferably 180-220° C., the reaction pressure is preferably 0-1.0 Mpa.

In the fifth separation tower (9), the separation pressure is preferably 0.3-0.5 Mpa, and the separation temperature is preferably 50-100° C. The top of the fifth separation tower (9) is preferably cooled with a coolant, and the temperature of the coolant is preferably −10-−30° C.

Fluorination catalysts for use with embodiments of the invention preferably are iron-containing chromium oxofluoride catalysts. In the iron-containing chromium oxofluoride catalysts, chromium accounts for 80-100% based on the mass of the active metals. The iron-containing chromium oxofluoride catalysts may further comprise other active metals. Other active metals are preferably one, two, three, or four kinds of metals selected from Mg, Zn, Al, and La.

Isomerization catalysts for use with embodiments of the invention preferably are chromium oxofluoride catalysts and/or aluminum trifluoride catalysts.

The physical characteristics of catalysts for use with embodiments of the invention preferably are not important. For example, the shapes of these catalysts may include spheres, flakes, and granules. Although it is not necessary, these catalysts preferably are subjected to fluorination treatments prior to use, which for example may be pre-treatment with HF. This pre-treatment is thought to convert oxides on the surfaces of the catalysts into fluorides. This pre-treatment can be achieved with the catalysts and HF in a suitable catalyst reactor. This can be performed at a selected temperature, about 200-300° C., by passing anhydrous HF through the catalyst for 15-400 minutes. A method for such preparation may be found in Chinese Patent No. CN1408476.

To solve the problem that alkenes are prone to polymerize to form carbonization, in accordance with embodiments of the invention, an oxidative gas is passed into the reactor. A preferred oxidative gas is oxygen. The amount of the oxidative gas added is preferably 0.1-20% of the amount of HCC-240fa.

In accordance with embodiments of the invention, the reactors, distillation towers, and related material delivery tubes/pipes, discharge tubes, and related unties should be made of corrosion-resistant materials. Typical corrosion-resistant materials include Ni alloy, stainless steel, copper plated steel, etc.

EQUIPMENT

Figure 1:
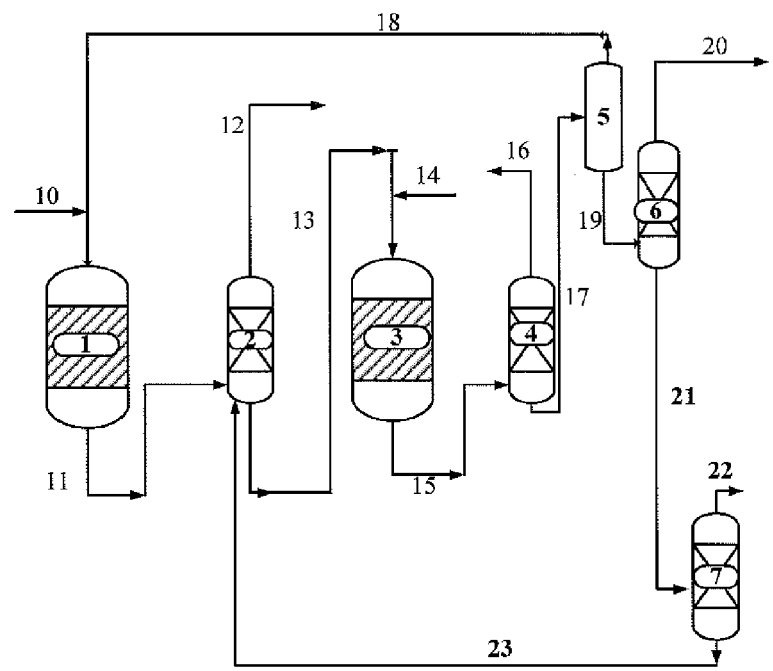
FIG. 1 illustrates a flowchart of a process of the invention, wherein the material flows are shown.
Figure 2:
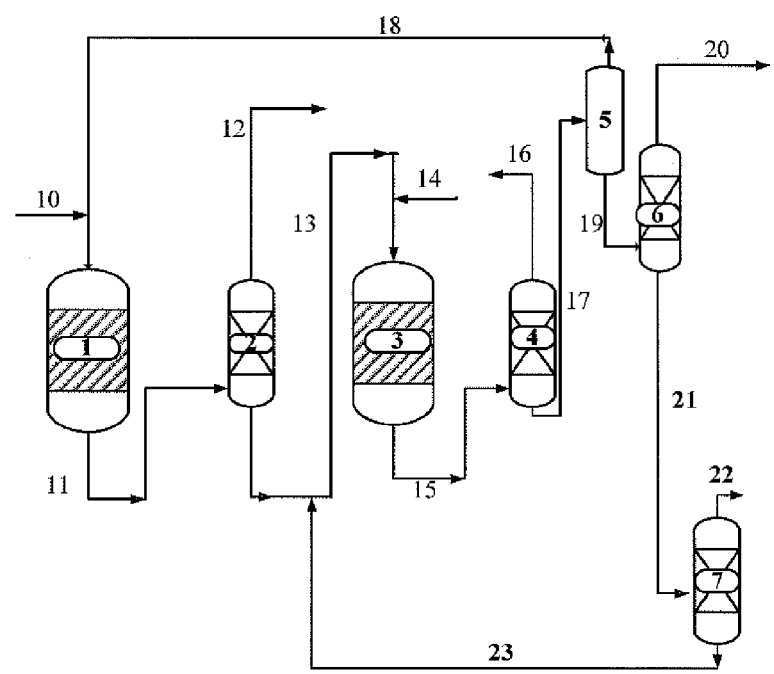
FIG. 2 illustrates a flowchart of a process of the invention, wherein the material flows are shown.
Figure 3:
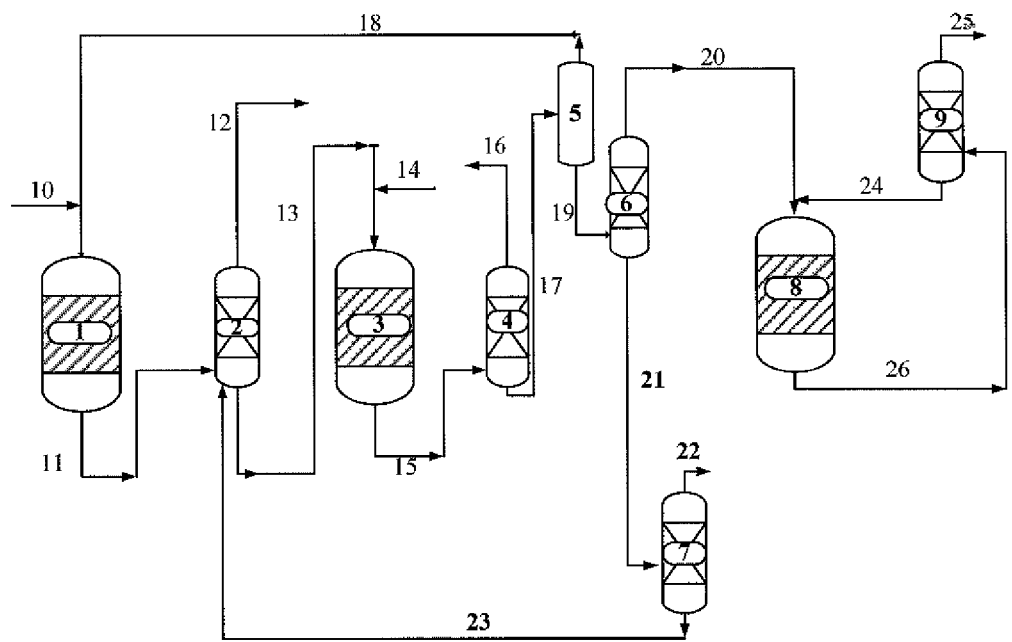
FIG. 3 illustrates a flowchart of a process of the invention, wherein the material flows are follows.

1. First reactor, 2. First separation tower, 3. Second reactor, 4. Second separation tower, 5. Static can, 6. Third separation tower, 7. Fourth separation tower, 8. Third reactor, 9. Fifth separation tower.

Material Flows (Material Streams):

10. Starting material stream containing anhydrous HF and HCC-240fa, 11. Reaction product stream, 12. HCl-containing material stream, 13. Material stream containing HFC-245fa, HCFC-1233zd and HF, 14. Oxidative gas, 15. Reaction product stream, 16. Material stream containing HCl and trans-HFO-1234ze, 17. Material stream containing cis-HFO-1234ze, HFC-245fa, HCFC-1233zd, HCFC-244fa and HF, 18. Material stream containing primarily HF, 19. Material stream containing cis-HFO-1234ze, HFC-245fa and HCFC-1233zd, 20. Material stream containing primarily cis-HFO-1234ze, 21. Material stream containing HFC-245fa and HCFC-1233zd, 22. Material stream containing HFC-245fa, 23. Material stream containing HCFC-1233zd, 24. Material stream containing cis-HFO-1234ze, 25. Material stream containing trans-HFO-1234ze, 26. Material stream containing trans-HFO-1234ze and cis-HFO-1234ze.

DETAILED DESCRIPTION

The invention will be further explained using the following examples. However, the scope of protection of the present invention is not limited by these examples. One skilled in the art should appreciate that the scope of the invention covers all possible embodiments in the claims, improved embodiments and equivalents thereof.

Example 1

Preparation of Gas Phase Fluorination Catalysts

Obtain hydroxyl compounds from a solution containing 1 g of $ZnCl_2$, 13 g of $Al(NO_3)_3 \cdot 9H_2O$, 1 g of $FeCl_3 \cdot 9H_2O$, and 360 g of 10% $CrCl_3$ solution by precipitation. Heat the precipitates, and then treat the precipitates with HF to obtain mixed metal fluoride salts. Add 15 ml of the mixed metals fluoride salts into a Monel alloy reactor. Pass chlorine gas for 4 hours at 400° C. Use nitrogen to remove residual chlorine gas. Then, lower the temperature to a temperature suitable for reaction and pass reaction material gas into the reactor to allow the reaction to occur.

Example 2

Co-Production of Trans-HFO-1234ze and HFC-245fa

Use a stainless steel tube (050 mm; 50 mm diameter) as a first reactor (1). Charge a catalyst prepared in Example 1 into the first reactor (1). The reaction conditions are controlled as follows: reaction temperature 200° C., reaction pressure 0.4 Mpa, space speed (volume displacement) 6000, molar ratio of 240fa:HF:$O_2$=1:10:0.03. The selectivities of products in the product stream (11) thus produced are: HFO-1233zd (91.32%), HFO-1234ze (1.06%), HFC-245fa (4.90%), HCFC-244fa (2.72%). HCC-240fa conversion rate is 95.8%.

Introduce the product stream (11) into the first separation tower (2) to separate the components. The boiler of the separation tower has a volume of 30 L, a diameter of 25 mm, and a height of 5.6 m. The operation conditions are controlled at: boiler temperature 70° C., pressure 0.4 Mpa, and coolant temperature −30° C. After separation, the material stream (12) formed at the top of the separation tower contains the major compositions with the following molar contents: HCl (97.32%), HFO-1233zd (1.0%), and HF (0.90%). The material stream (13) formed at the boiler of the separation tower has the major compositions with the following molar contents: HF (89.2%), HFO-1233zd (9.12%), and HFC-245fa (0.89%).

Introduce the material stream (13) into the second reactor (3). Add a catalyst from Example 1 into the second reactor (3). Control the reaction conditions as follows: reaction temperature 360° C., reaction pressure 0.3 Mpa, space speed 400 $h^{-1}$, and a molar ratio of the organic phase to oxygen 1:0.05. In the product stream (15) thus formed, the major compositions have the molar contents: E-HFO-1234ze (48.15%), Z-HFO-1234ze (21.01%), E-HFO-1233zd (13.97%), Z-HFO-1233zd (3.59%), HFC-245fa (11.62%), and HCFC-244fa (1.51%).

Introduce the product stream (15) into the second separation tower (4) to conduct separation. The separation conditions are controlled as follows: boiler temperature 70° C., pressure 0.3 Mpa, and coolant temperature −30° C. In the material stream (16) formed at the top of the separation tower, the major compositions have the molar contents: E-HFO-1234ze (33.2%), Z-HFO-1234ze (8.56%), and HCl (55%). In the material stream (19) formed in the boiler of the separation tower, the major compositions have the molar contents: HF (87.4%), E-HFO-1234ze (0.45%), Z-HFO-1234ze (2.06%), HFC-245fa (1.99%), E-HFO-1233zd (5.4%), and Z-HFO-1233zd (1.90%).

Introduce the material stream (19) from the boiler into the third separation tower (6) to conduct separation. Separation conditions are controlled as follows: boiler temperature 70° C., pressure 0.5 Mpa, and coolant temperature at the top of the tower 0° C. In the material stream (20) formed at the top of the tower, major compositions have the molar contents: Z-HFO-1234ze (99.10%). In the material stream (21) formed at the bottom of the tower, major compositions have the molar contents: HFC-245fa (25.17%), E-HFO-1233zd (52.3%), and Z-HFO-1233zd (12.89%).

Introduce the material stream (21) from the bottom of the tower into the fourth separation tower (7) to conduct separation. The separation conditions are controlled as follows: boiler temperature 70° C., pressure 0.5 Mpa, and coolant temperature at the top of the tower 15° C. At the top of the tower, the material stream (22) thus formed comprises mainly HFC-245fa, wherein the molar content of HFC-245fa accounts for 99.26% of the total material stream (22). At the boiler, a material stream (23) is formed, the molar contents of major compositions in which are: E-HFO-1233zd (78.3%), and Z-HFO-1233zd (19.33%).

Add the material stream (20) from the top of the third separation tower (6) into the third reactor (8) to perform isomerization. The reaction temperature is 200° C. The material space speed is 80 $h^{-1}$. In the material streamed formed in the boiler, the major compositions have the molar contents: E-HFO-1234ze (85.5%) and Z-HFO-1234ze (14.5%).

Introduce the material stream (26) from the bottom of the third reactor (8) into the fifth separation tower (9). The separation conditions are: tower boiler temperature 70° C., pressure 0.5 Mpa, and the coolant temperature at the top of the tower −20° C. The material stream (25) obtained from the top of the tower contains trans-HFO-1234ze, wherein the molar contents of trans-HFO-1234ze, relative to the total of material stream (25), is 99.94%. At the bottom of the tower, a material stream (4) is obtained, the molar content of the major composition, Z-HFO-1234ze, is 98.36%.

Example 3

Preparation of HCFC-1233zd

In a stainless steel tube (Ø50 mm), a catalyst from Example 1 (after treatment as shown in Example 1) is introduced. The filling amount is 50 ml. First, pass HCC-240fa, anhydrous HF and $O_2$ through a preheating can, at 220° C., to thoroughly preheat the mixture. Then, introduce the mixture into the reactor to carry out the reaction. The molar ratio of anhydrous HF, HCC-240fa and oxygen is 10:1:0.02, the space speed is 700 $h^{-1}$, the reaction temperature is 180-260° C., and the reaction pressure is 0.3 Mpa. The product stream leaving the reactor is analyzed with GC-MS, and the results are summarized in TABLE 1.

TABLE 1

Temperature Comparison

| Reaction Temperature | HCC-240fa Conversion Rate | Outlet Product Selectivity | | | |
|---|---|---|---|---|---|
| | | HFO-1233zd | HFO-1234ze | HFC-245fa | HCFC-244fa |
| 180° C. | 87% | 93.44% | 0.75% | 1.56% | 4.25% |
| 200° C. | 94.5% | 91.5% | 1.25% | 3.74% | 3.51% |
| 220° C. | 96.2% | 90.68% | 1.46% | 4.82% | 3.04% |
| 240° C. | 96.4% | 81.55% | 1.35% | 14.26% | 2.84% |
| 260° C. | 96.8% | 75.64% | 1.52% | 20.78%% | 2.06% |

Example 4

Preparation of HCFC-1233zd

In a stainless steel tube (Ø50 mm), a catalyst from Example 1 (after treatment as shown in Example 1) is introduced. The filling amount is 50 ml. First, pass HCC-240fa and anhydrous HF through a preheating can, at 220° C., to mix and preheat the mixture. Then, introduce the mixture into the reactor to carry out the reaction. The reaction temperature is 220° C., space speed is 700 h$^{-1}$, and the reaction pressure is 0.3 Mpa. The molar ratios of HF and HCC-240fa are varied. The product stream leaving the reactor is analyzed with GC-MS, and the results are summarized in TABLE 2.

TABLE 2

Ratios of Materials

| HF: 240fa:O$_2$ Molar Ratio | 240fa conversion rate % | Outlet Product Selectivities | | | |
|---|---|---|---|---|---|
| | | HFO-1233zd | HFO-1234ze | HFC-245fa | HCFC-244fa |
| 3:1:0.005 | 43.2%% | 98.75% | 0.30% | 0.54% | 0 |
| 6:1:0.005 | 77.45% | 96.40% | 0.81% | 1.54% | 1.25% |
| 9:1:0.005 | 95.8% | 90.94% | 1.40% | 4.62% | 3.04% |
| 12:1:0.005 | 96.2% | 89.72% | 4.45% | 2.89% | 2.94% |
| 15:1:0.005 | 97.1% | 89.69% | 5.14% | 3.04% | 2.13% |
| 18:1:0.005 | 98.2% | 89.77% | 5.21% | 2.98% | 2.04% |

Example 5

Preparation of HCFC-1233zd

In a stainless steel tube (Ø50 mm), a catalyst from Example 1 (after treatment as shown in Example 1) is introduced. The filling amount is 50 ml. First, pass HCC-240fa, anhydrous HF and O$_2$ through a preheating can, at 220° C., to thoroughly preheat the mixture. Then, introduce the mixture into the reactor, at different space speeds, to carry out the reaction. The reaction temperature is 22° C., the molar ratio of anhydrous HF, HCC-240fa and oxygen is 10:1:0.005, and the reaction pressure is 0.3 Mpa. The results are summarized in TABLE 3.

TABLE 3

Reaction Space Speed Comparison

| Space Speed (h$^{-1}$) | 240fa conversion rate % | Outlet Product Selectivities | | | |
|---|---|---|---|---|---|
| | | HFO-1233zd | HFO-1234ze | HFC-2451a | HCFC-244fa |
| 300 | 99.12% | 93.08% | 3.78% | 1.58% | 1.56% |
| 400 | 98.65% | 93.53% | 3.04% | 1.67% | 1.76% |
| 500 | 98.10% | 92.52% | 2.45% | 2.89% | 2.14% |
| 600 | 97.30% | 91.68% | 1.79% | 3.77% | 2.76% |
| 700 | 96.20% | 90.68% | 1.46% | 4.82% | 3.04% |
| 800 | 90.15% | 90.42% | 0.97% | 5.14% | 3.47% |

Example 6

Preparation of HCFC-1233zd

In a stainless steel tube (Ø50 mm), a catalyst from Example 1 (after treatment as shown in Example 1) is introduced. The filling amount is 50 ml. First, pass HCC-240fa, anhydrous HF and O$_2$ through a preheating can, at 220° C., to thoroughly preheat the mixture. Then, introduce, at different temperatures, the mixture into the reactor to carry out the reaction. The reaction temperature is 220° C., the molar ratio of anhydrous HF, HCC-240fa and oxygen is 10:1:0.005, and the space speed is 700 h$^{-1}$. The results are summarized in TABLE 4.

TABLE 4

Reaction Pressure Comparison

| Reaction Pressure (MPa) | HCC-240fa Conversion rate (%) | Outlet Product Selectivities | | | |
|---|---|---|---|---|---|
| | | HFO-1233zd | HFO-1234ze | HFC-245fa | HCFC-244fa |
| 0.2 | 96.3% | 91.66% | 3.05% | 3.84% | 1.45% |
| 0.3 | 96.2% | 90.68% | 1.46% | 4.82% | 3.04% |
| 0.4 | 96.4% | 90.32% | 1.02% | 5.51% | 3.15% |
| 0.5 | 96.5% | 89.22% | 0.49% | 7.22% | 3.07% |

Example 7

Preparation of HFO-1234ze

In a stainless steel tube (Ø50 mm) as the second reactor (3), a catalyst from Example 1 (after treatment as shown in Example 1) is introduced. The filling amount is 50 ml. First, a material stream (13) containing HCC-240fa and HF formed at the boiler of the first separation tower is passed, together with O$_2$, through a preheating can, at 300° C., to thoroughly preheat the mixture. Then, introduce, at different temperatures, the mixture into the second reactor (3) to carry out the reaction. The molar ratio of the organic phase to oxygen is 1:0.005, the space speed is 400 h$^{-1}$, and the reaction pressure is 0.3 Mpa. Results from reaction temperature comparison are summarized in TABLE 5.

TABLE 5

Reaction Temperature Comparison

| Organic phase composition (mol %) | | Reaction Temperature | Molar contents of compositions from outlet (%) | | | | | |
|---|---|---|---|---|---|---|---|---|
| | | | HFO-1234ze | | HFO-1233zd | | HFC- | HCFC- |
| | | | E | Z | E | Z | 245fa | 244fa |
| HF | 91.89, | 300° C. | 20.17 | 6.49 | 37.23 | 15.94 | 18.47 | 1.70 |
| 1234ze | 0.40 | 320° C. | 33.19 | 12.24 | 19.64 | 10.76 | 11.97 | 0.41 |
| 1233zd | 6.58, | 340° C. | 40.05 | 16.35 | 23.15 | 6.28 | 12.35 | 1.82 |
| 245fa | 0.88, | 360° C. | 48.15 | 21.01 | 13.97 | 3.59 | 11.62 | 1.51 |
| HCl | 0.04 | 380° C. | 48.35 | 21.54 | 13.02 | 3.42 | 11.52 | 1.15 |
| 244fa | 0.21 | | | | | | | |

Example 8

Preparation of HFO-1234ze

In a stainless steel tube (050 mm) as the second reactor (3), a catalyst from Example 1 (after treatment as shown in Example 1) is introduced. The filling amount is 50 ml. First, a material stream (13) containing HCC-240fa and HF formed at the boiler of the first separation tower is passed, together with $O_2$, through a preheating can, at 300° C., to thoroughly preheat the mixture. Then, introduce, at different temperatures, the mixture into the second reactor (3) to carry out the reaction. The molar ratio of the organic phase to oxygen is 1:0.005, the space speed is 400 $h^{-1}$, and the reaction temperature is 360° C. Results from reaction pressure comparison are summarized in TABLE 6.

TABLE 6

Reaction Pressure Comparison

| Organic Phase Composition (mol %) | | Reaction Pressure MPa | Molar contents of compositions from outlet (%) | | | | | |
|---|---|---|---|---|---|---|---|---|
| | | | HFO-1234ze | | HFO-1233zd | | HFC- | HCFC- |
| | | | E | Z | E | Z | 245fa | 244fa |
| HF | 91.67 | 0.2 | 49.07 | 22.42 | 13.84 | 3.67 | 10.24 | 0.76 |
| 1234ze | 0.54 | 0.3 | 48.15 | 21.01 | 13.97 | 3.59 | 11.62 | 1.51 |
| 1233zd | 7.28 | 0.4 | 42.05 | 16.04 | 13.05 | 3.47 | 23.85 | 2.82 |
| 245fa | 0.16 | 0.5 | 37.29 | 13.48 | 13.04 | 3.06 | 30.09 | 3.04 |
| HCl | 0.06 | 0.6 | 31.05 | 10.94 | 13.16 | 3.48 | 38.52 | 2.85 |
| 244fa | 0.29 | | | | | | | |

Example 9

Operation of the First Separation Tower (2), Separation of HCl

Introduce the product stream (11) formed in the first reaction into the first separation tower (2) to fractionate the components. In the product stream (11), the major compositions molar contents are: HF (45.1%), HO (48.94%), HCFC-1233zd (5.06%), and other organic phase (5.96%). Separation efficiencies under different temperatures and pressures are shown in TABLE 7.

TABLE 7

Separation of the first separation tower

| Boiler temperature (° C.) | Pressure (MPa) | Coolant temperature at the top (° C.) | Molar contents in the compositions from top (%) | | |
|---|---|---|---|---|---|
| | | | HF | HCl | 其他 |
| 60 | 0.3 | −30 | 1.91 | 96.34 | 1.75 |
| | 0.4 | | 0.94 | 97.25 | 1.81 |
| | 0.5 | | 0.89 | 97.46 | 1.65 |
| 60 | 0.4 | −30 | 0.94 | 97.25 | 1.81 |
| 70 | | | 2.94 | 90.16 | 6.9 |
| 80 | | | 5.04 | 82.27 | 12.69 |
| 60 | 0.4 | −20 | 4.05 | 86.02 | 9.93 |
| | | −30 | 0.94 | 97.25 | 1.81 |
| | | −40 | 0.25 | 98.45 | 1.3 |

Example 10

Operation of the Second Separation Tower, Separation of Trans-HFO-1234Ze

Introduce the product stream (15) from the second reactor into the second separation tower (4) to perform separation. In the product stream (15), the molar contents of major compositions are: HF (44.15%), HCl (27.78%), HFO-1234ze (22.14%), HCFC-1233zd (4.41%), and HFC-245fa (1.25%). Separation efficiencies under different temperatures and pressures are summarized in TABLE 8.

TABLE 8

Separation at the second separation tower (4)

| Boiler Temperature (° C.) | Pressure (MPa) | Coolant temperature (° C.) | Molar contents of compositions from the top (%) | | | |
|---|---|---|---|---|---|---|
| | | | E-HFO-1234ze | Z-HFO-1234ze | E-HFO-1233zd | HFC-245fa |
| 50 | 0.3 | −40 | 97.91 | 0.21 | 1.34 | 0.54 |
| | 0.4 | | 98.52 | 0.16 | 1.03 | 0.29 |
| | 0.5 | | 99.15 | 0.08 | 0.64 | 0.13 |
| 50 | 0.4 | −40 | 98.52 | 0.16 | 1.03 | 0.29 |
| 60 | | | 94.32 | 0.69 | 3.79 | 1.05 |
| 70 | | | 89.77 | 1.01 | 6.25 | 2.97 |
| 50 | 0.4 | −30 | 95.59 | 0.48 | 2.85 | 0.96 |
| | | −40 | 98.52 | 0.16 | 1.03 | 0.29 |
| | | −50 | 99.04 | 0.09 | 0.83 | 0.04 |

Example 11

Operation of the Third Separation Tower (6), Separation of Cis-HFO-1234Ze

Introduce the product stream (19) from static can (5) into the third separation tower to perform separation. In the product stream (19), the molar contents of major compositions are: Z-HFO-1234ze (49.87%), Z-HFO-1233zd (26.51%), E-HFO-1233zd (6.46%), and HFC-245fa (12.67%). The separation efficiencies under different temperatures and pressures are summarized in TABLE 9.

TABLE 9

Separation efficiency of the third separation tower (6)

| Boiler temperature (°C) | Pressure (MPa) | Coolant temperature (°C) | Molar contents of organic phase at the top (%) | | | |
|---|---|---|---|---|---|---|
| | | | E-HFO-1234ze | Z-HFO-1233zd | E-HFO-1233zd | HFC-245fa |
| 70 | 0.3 | 0 | 94.85 | 3.49 | 0.40 | 1.26 |
| | 0.4 | | 97.06 | 2.04 | 0.16 | 0.74 |
| | 0.5 | | 99.10 | 0.71 | 0.03 | 0.16 |
| 70 | 0.5 | 0 | 99.10 | 0.71 | 0.03 | 0.16 |
| 80 | | | 98.25 | 1.34 | 0.12 | 0.29 |
| 90 | | | 97.36 | 1.97 | 0.19 | 0.48 |
| 70 | 0.5 | 10 | 91.04 | 6.21 | 0.69 | 2.06 |
| | | 0 | 99.10 | 0.71 | 0.03 | 0.16 |
| | | −10 | 99.26 | 0.62 | 0.02 | 0.10 |

Example 12

Operation of the Fourth Separation Tower (7), Separation of HFC-245Fa

Introduce the product stream (21) from the third separation tower (6) into the fourth separation tower (7) to perform separation. In the product stream (21) formed at the boiler, the molar contents of the major compositions are: HFC-245fa (50.82%), Z-HFO-1233zd (39.42%), and E-HFO-1233zd (9.76%). Separation efficiencies at different temperatures and pressures are summarized in TABLE 10.

TABLE 10

Separation efficiencies of the fourth separation tower (7)

| Boiler temperature (°C) | Pressure (MPa) | Coolant temperature (°C) | Molar contents of organic phase at the top (%) | | |
|---|---|---|---|---|---|
| | | | HFC-245fa | E-HFO-1233zd | Z-HFO-1233zd |
| 70 | 0.3 | 15 | 95.35 | 3.49 | 1.16 |
| | 0.4 | | 97.94 | 1.28 | 0.78 |
| | 0.5 | | 99.26 | 0.53 | 0.21 |
| 70 | 0.5 | 15 | 99.26 | 0.53 | 0.21 |
| 80 | | | 97.35 | 1.79 | 0.86 |
| 90 | | | 94.29 | 3.97 | 1.74 |
| 70 | 0.5 | 20 | 92.34 | 6.49 | 1.17 |
| | | 15 | 99.26 | 0.53 | 0.21 |
| | | 10 | 99.40 | 0.46 | 0.14 |

Example 13

Isomerization of cis-1234ze to Produce trans-1234ze

Control the reaction pressure in the third reactor (8) at 0.4 Mpa. In the material stream (20) added to the third reactor (8), the molar contents of the major compositions are: Z-HFO-1234ze (99.10%), Z-HFO-1233zd (0.71%), E-HFO-1233zd (0.03%), and HFC-245fa (0.16%). Under different temperatures and different space speeds, the molar contents of the major compositions in the material stream (26) are as shown in TABLE 11.

TABLE 11

Comparison in the third reactor (8)

| Reactor temperature (°C) | Space speed (h⁻¹) | Molar contents of organic phase at reactor outlet (%) | |
|---|---|---|---|
| | | E-HFO-1234ze | Z-HFO-1234ze |
| 180 | 80 | 69.0 | 31.0 |
| 200 | | 85.5 | 14.5 |
| 220 | | 84.9 | 15.1 |
| 200 | 60 | 85.7 | 14.3 |
| | 80 | 85.5 | 14.5 |
| | 100 | 79.6 | 20.4 |

Example 14

The Fifth Separation Tower (9), Separation of E-1234Ze

Add material stream (26) into the fifth separation tower (9) to perform separation. In the material stream (26), the molar contents of the major compositions are: E-HFO-1234ze (85.5%) and Z-HFO-1234ze (14.5%). Separation data are shown in TABLE 12.

TABLE 12

Separation in the fifth separation tower

| Boiler temperature (°C) | Coolant temperature (°C) | Molar contents of the organic phase at the reactor outlet (%) | |
|---|---|---|---|
| | | E-HFO-1234ze | Z-HFO-1234ze |
| 60 | −20 | 94.67 | 5.33 |
| 70 | | 99.94 | 0.06 |
| 80 | | 99.95 | 0.05 |
| 70 | −30 | 99.95 | 0.05 |
| | −20 | 99.94 | 0.06 |
| | −10 | 86.98 | 13.02 |

What is claimed is:

1. A method for co-producing HFO-1234ze and HFC-245fa, characterized in that the method comprises the following steps:

(1) adding into a first reactor (1) a starting material stream (10) that contains anhydrous HF and HCC-240fa, and in the presence of an oxidative gas and the action of a fluorination catalyst, reacting the anhydrous HF and HCC-240fa to produce a product stream (11);

(2) adding the product stream (11) into a first separation tower (2) to form a material stream (12) that contains HCL at the top of the first separation tower and a material stream (13) that contains HFC-245fa, HCFC-1233zd and HF in a boiler of the first separation tower;

(3) introducing the material stream (13) into a second reactor (3) and simultaneously introducing into the second reactor (3) an oxidative gas to react, under the action of a fluorination catalyst, and form a product stream (15);

(4) introducing the product stream (15) into a second separation tower (4) to form a material stream (16) containing HCL and trans-HFO-1234ze at the top of the second separation tower, and a material stream (17) containing cis-HFO-1234ze, HFC-245fa, HCFC-1233zd, HCFC-244fa and HF in the boiler of the second separation tower, wherein the material stream (16), after washing with water, separation, and drying, produces trans-HFO-1234ze;

(5) introducing the material stream (17) into a static can (5); after layer separation, circulating the upper layer, material stream (18) comprising primarily HF, back into the first reactor (1), wherein the lower layer organic phase forming material stream (19) that comprises cis-HFO-1234ze, HFC-245fa and HCFC-1233zd;

(6) introducing the material stream (19) into a third separation tower (6), wherein a material stream (20) forms at the top of the third separation tower and contains primarily cis-HFO-1234ze, and a material stream (20) formed in the boiler of the third separation tower comprises HFC-245fa and HCFC-1233zd, wherein the material stream (20) is isomerized to produce trans-HFO-1234ze;

(7) introducing the material stream (21) into a fourth separation tower, wherein a material stream (22) formed at the top of the fourth separation tower comprises HFC-245fa, and a material stream (23) formed in the boiler of the fourth separation tower comprise HCFC-1233zd, wherein the material stream (23) is circulated back into the first separation tower (2) or the second reactor (3).

2. The method for co-producing HFO-1234ze and HFC-245fa according to claim 1, characterized in that in the first reactor (1), a reaction temperature is 200-250° C., a reaction pressure is 0.2-0.8 Mpa, a molar ratio of HF to HCC-240fa is from 3:1 to 18:1, and a space speed is 300-1000 $h^{-1}$.

3. The method for co-producing HFO-1234ze and HFC-245fa according to claim 2, characterized in that in the first reactor (1), a reaction temperature is 180-260° C., a reaction pressure is 0.2-0.5 Mpa, a molar ratio of HF to HCC-240fa is from 6:1 to 18:1, and a space speed is 300-800 $h^{-1}$.

4. The method for co-producing HFO-1234ze and HFC-245fa according to claim 1, characterized in that in the second reactor (3), a reaction temperature is 300-380° C., a reaction pressure is 0.2-0.8 Mpa, a molar ratio of HF to HCC-240fa is from 3:1 to 8:1, and a space speed is 300-800 $h^{-1}$.

5. The method for co-producing HFO-1234ze and HFC-245fa according to claim 1, characterized in that in the first separation tower (2), a separation pressure is 0.2-0.8 Mpa and a separation temperature is 50-100° C.

6. The method for co-producing HFO-1234ze and HFC-245fa according to claim 5, characterized in that in the first separation tower (2), a separation pressure is that same as that in the first reaction (1), wherein the separation pressure in the first separation tower is 0.3-0.5 Mpa and a separation temperature is 60-80° C.

7. The method for co-producing HFO-1234ze and HFC-245fa according to claim 5, characterized in that a coolant is used at the top of the first separation tower (2), wherein a temperature of the coolant is −40-−20° C.

8. The method for co-producing HFO-1234ze and HFC-245fa according to claim 1, characterized in that in the second separation tower (4), a separation pressure is 0.2-0.8 Mpa and a separation temperature is 50-90° C.

9. The method for co-producing HFO-1234ze and HFC-245fa according to claim 8, characterized in that in the second separation tower (4), a separation pressure is that same as that in the first reaction (1), wherein the separation pressure in the second separation tower (4) is 0.3-0.5 Mpa and a separation temperature is 50-70° C.

10. The method for co-producing HFO-1234ze and HFC-245fa according to claim 8, characterized in that a coolant is used at the top of the second separation tower (4), wherein a temperature of the coolant is −50-−30° C.

11. The method for co-producing HFO-1234ze and HFC-245fa according to claim 1, characterized in that in the third separation tower (6), a separation pressure is 0.1-1.2 Mpa and a separation temperature is 50-100° C.

12. The method for co-producing HFO-1234ze and HFC-245fa according to claim 11, characterized in that a coolant is used at the top of the third separation tower (6), wherein a temperature of the coolant is 0-20° C.

13. The method for co-producing HFO-1234ze and HFC-245fa according to claim 1, characterized in that in the fourth separation tower (7), a separation pressure is 0.2-0.9 Mpa and a separation temperature is 60-110° C.

14. The method for co-producing HFO-1234ze and HFC-245fa according to claim 13, characterized in that a coolant is used at the top of the fourth separation tower (7), wherein a temperature of the coolant is 10-18° C.

15. The method for co-producing HFO-1234ze and HFC-245fa according to claim 1, characterized in that the material stream (20) introduced into the third reactor (8) is isomerized, in the presence of an isomerization catalyst, to produce a material stream (24) containing trans-HFO-1234ze and cis-HFO-1234ze, wherein the material stream (26) is introduced into a fifth separation tower (9), wherein a material stream (25) formed at the top of the fifth separation tower contains trans-HFO-1234ze, and a material stream (24) formed in the boiler of the fifth separation tower contains cis-HFO-1234ze, wherein the material stream (24) is circulated back into the third reactor (8).

16. The method for co-producing HFO-1234ze and HFC-245fa according to claim 15, characterized in that in the third reactor (8), a reaction temperature is 180-220° C. and a reaction pressure is 0-1.0 Mpa.

17. The method for co-producing HFO-1234ze and HFC-245fa according to claim 15, characterized in that in the fifth separation tower (9), a separation pressure is 0.3-0.5 Mpa and a separation temperature is 50-100° C.

18. The method for co-producing HFO-1234ze and HFC-245fa according to claim 15, characterized in that a coolant is used at the top of the fifth separation tower (9), a temperature of the coolant is −10-−30° C.

19. The method for co-producing HFO-1234ze and HFC-245fa according to claim 1, characterized in that the fluorination catalyst used in the first reactor (1) and the second reactor (5) is an iron-containing chromium oxofluoride catalyst.

20. The method for co-producing HFO-1234ze and HFC-245fa according to claim 19, characterized in that in the iron-containing chromium oxofluoride catalyst, chromium accounts for 80-100% by mass of active metal.

21. The method for co-producing HFO-1234ze and HFC-245fa according to claim 20, characterized in that the iron-containing chromium oxofluoride catalyst contains one, two, three, or four types of metals selected from the group consisting of Mg, Zn, Al, and La.

22. The method for co-producing HFO-1234ze and HFC-245fa according to claim 15, characterized in that the isomerization catalyst used in the third reactor (8) is a chromium oxofluoride catalyst and/or an aluminum trifluoride catalyst.

23. The method for co-producing HFO-1234ze and HFC-245fa according to claim 1, characterized in that the oxidative gas is oxygen.

24. The method for co-producing HFO-1234ze and HFC-245fa according to claim 1, characterized in that the oxidative gas is added at an amount of 0.1-20% of HCC-240fa.

* * * * *